United States Patent
Rosato et al.

(10) Patent No.: US 10,933,133 B2
(45) Date of Patent: Mar. 2, 2021

(54) ANTI-BARF1 MONOCLONAL ANTIBODY

(71) Applicant: UNIQUEST PTY LIMITED, St. Lucia (AU)

(72) Inventors: Antonio Rosato, Campodarsego (IT); Riccardo Turrini, Albignasego (IT); Riccardo Dolcetti, Cordenons (IT); Debora Martorelli, Maniago (IT); Damiana Antonia Fae, Treviso (IT)

(73) Assignee: Uniquest Pty Limited, Queensland (AU)

( * ) Notice: Subject to any disclaimer, the term of this patent is extended or adjusted under 35 U.S.C. 154(b) by 199 days.

(21) Appl. No.: 15/773,296

(22) PCT Filed: Nov. 4, 2016

(86) PCT No.: PCT/EP2016/076691
§ 371 (c)(1),
(2) Date: May 3, 2018

(87) PCT Pub. No.: WO2017/077047
PCT Pub. Date: May 11, 2017

(65) Prior Publication Data
US 2018/0318418 A1 Nov. 8, 2018

(30) Foreign Application Priority Data
Nov. 4, 2015 (IT) .................. 102015000069010

(51) Int. Cl.
| | | |
|---|---|---|
| *C07K 16/00* | (2006.01) | |
| *A61K 39/395* | (2006.01) | |
| *C07K 16/08* | (2006.01) | |
| *G01N 33/569* | (2006.01) | |
| *G01N 33/574* | (2006.01) | |
| *C07K 14/005* | (2006.01) | |
| *A61P 35/00* | (2006.01) | |
| *A61K 39/12* | (2006.01) | |
| *C12N 15/63* | (2006.01) | |
| *A61K 39/00* | (2006.01) | |

(52) U.S. Cl.
CPC ........ *A61K 39/39558* (2013.01); *A61K 39/12* (2013.01); *A61K 39/395* (2013.01); *A61P 35/00* (2018.01); *C07K 14/005* (2013.01); *C07K 16/085* (2013.01); *C12N 15/63* (2013.01); *G01N 33/56994* (2013.01); *G01N 33/57484* (2013.01); *A61K 2039/585* (2013.01); *A61K 2039/6081* (2013.01); *C07K 2317/73* (2013.01); *C07K 2317/732* (2013.01); *C07K 2317/734* (2013.01); *C12N 2710/16222* (2013.01); *C12N 2710/16234* (2013.01)

(58) Field of Classification Search
CPC ... A61K 39/39558; A61P 35/00; C12N 15/63; C07K 14/005; G01N 33/57484
See application file for complete search history.

(56) References Cited

U.S. PATENT DOCUMENTS

2011/0135642 A1* 6/2011 Ooka .................. C07K 16/085
424/133.1

FOREIGN PATENT DOCUMENTS

| AU | 2009245587 B2 | 11/2009 |
|---|---|---|
| WO | WO-2002/060930 A2 | 8/2002 |
| WO | WO-2010/015704 | 2/2010 |
| WO | WO-2013/088114 | 6/2013 |
| WO | WO-2014/049087 | 4/2014 |
| WO | WO2014049087 * | 4/2014 |

OTHER PUBLICATIONS

Hoebe et al, Clin Vac and Immune Vo 18: 298-304, 2011 (Year: 2011).*
International Search Report for International Application No. PCT/EP2016/076691, dated Nov. 5, 2017, 6 pages.
Written Opinion of the International Searching Authority for International Application No. PCT/EP2016/076691, dated Nov. 5, 2017, 6 pages.
Turrini "Targeting BARF1 for the Therapeutic Control of EBV-Associated Malignancies," retrieved from the internet http://paduaresearch.cab.unipd.it/2562/1/tesi_Turrini_Riccardo.pdf, (retrieved Jun. 25, 2016); 81 pages.
Sall, et al., "Mitogenic Activity of Epstein-Barr Virus-Encoded BARF1 Protein," Oncogene, 23(28):4938-4944 (2004).
Decaussin, et al., "Expression of BARF1 Gene Encoded by Epstein-Barr Virus in Nasopharyngeal Carcinoma Biopsies," Cancer Research, American Association for Cancer Research, US., 60(19):5584-5588 (2000).
Sheng, et al., "N-Terminal Domain of BARF1 Gene Encoded by Epstein-Barr Virus is Essential for Malignant Transformation of Rodent Fibroblasts and Activation of BCL-2", Oncogene, Nature Publishing Group, 20(10):pp. 1176-1185 (2001).
Huan, et al., "Chimeric Antigen Receptor for Adoptive Immunotherapy of Cancer: Latest Research and Future Prospects," Molecular Cancer, Biomed Central, 13(1):219 (2014).

* cited by examiner

*Primary Examiner* — Lei Yao
(74) *Attorney, Agent, or Firm* — Nixon & Vanderhye, PC

(57) ABSTRACT

The present invention relates to a new anti-BARF1 monoclonal antibody.

12 Claims, 5 Drawing Sheets

Specification includes a Sequence Listing.

Fig. 1a
MARFIAQLLLLASCVAAGQAVTAFLGERVT
LTSYWRRVSLGPEIEVSWSKLGPGEEQVLI
GRMHHDIFIEWPFRGFFDIHRSANTFFLV
VTAANISHDGNYLCRMKLGETEVTKQEHLS
VVKPLTLSVHSERSQFPQFSVLTVTCTVNA
FPHPHVQWLMPEGVEPAPTAANGGVMKEKD
GSLSVAVDLSLPHPWHLPVTCVGKNDKEEA
HGYVSGYLSQ
Fig. 1b
05/08 CVGKNDKEEAHVGYVSGYLSQ 
06/08 CRMKLGETEVTKQEHLS 
08/08 RVTLTSYWRRV 
08/08-1 RVTLTSYW 
08/08-2 TSYWRRV 
Fig. 1c
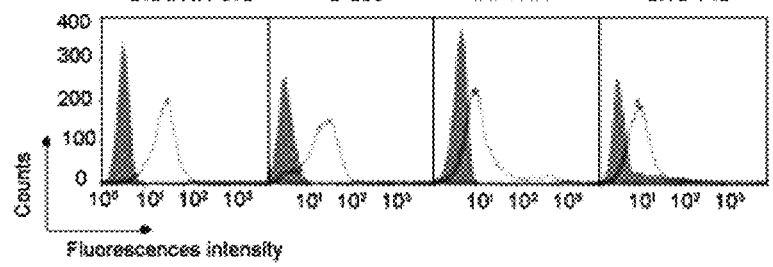
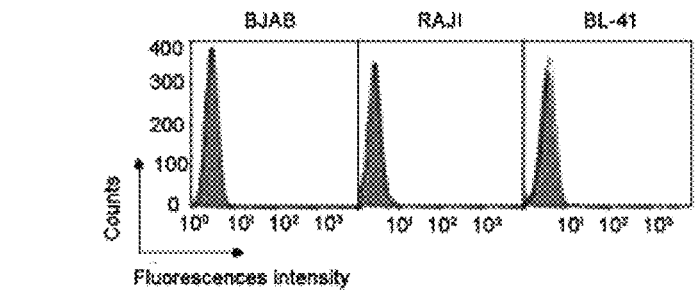
Fig. 1d
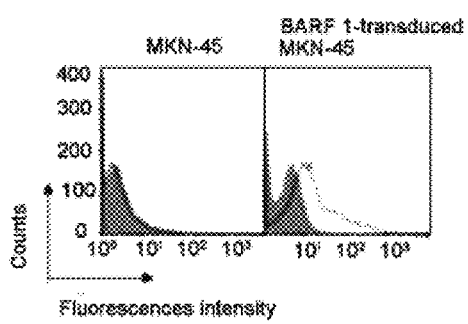

C-666
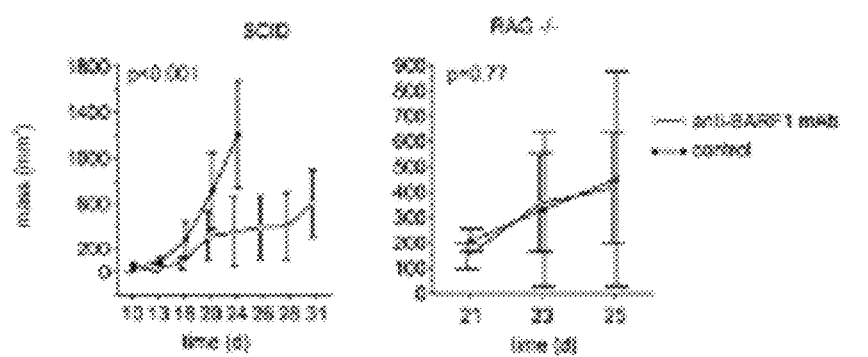
Fig. 4a
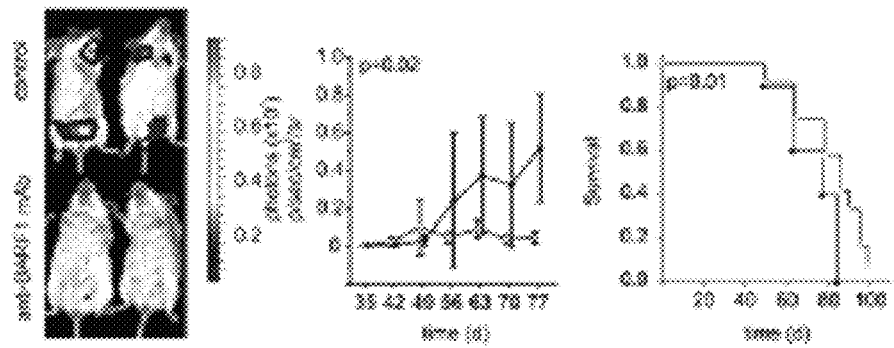
Fig. 4b
Fig. 4c

GRANTA-519
Fig. 5a
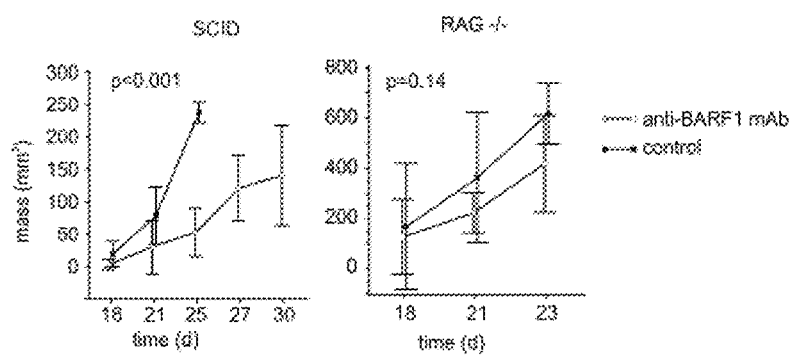
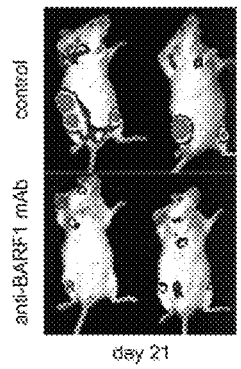
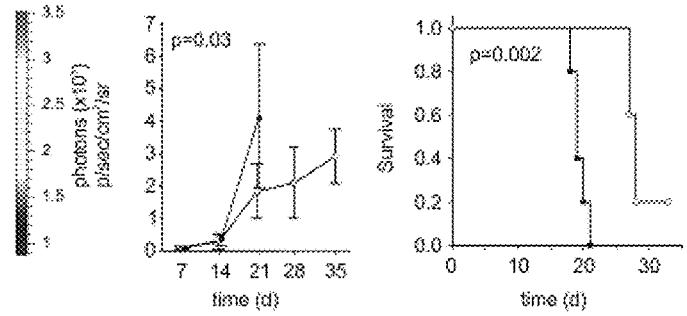
Fig. 5c      Fig. 5d      Fig. 5b

SEQUENCE LISTING

```
<160> NUMBER OF SEQ ID NOS: 26

<210> SEQ ID NO 1
<211> LENGTH: 508
<212> TYPE: DNA
<213> ORGANISM: Mus musculus

<400> SEQUENCE: 1
caccatgggc aggcttacat cctcattcct gctgctgatt gtccctgcat atgtcctttc      60
ccaggttact ctgaaagagt ctggccctgg gatattgcag ccctcccaga ccctcagtct     120
gacttgttct ttctctgggt tttcactgag cacttctggt atgggtgtga gctggattcg     180
tcagccttca ggaaagggtc tggagtggct ggcacacatt tactgggatg atgacaagcg     240
ctataaccca tccctgaaga gccggctcac aatctccaag gatacctcca gaaaccaggt     300
attcctcaag atcaccagtg tggacactgc agatactgcc acatactact gtgctcgaag     360
agatgggaca cggggtttg actactgggg ccaaggcacc actctcacag tctcctcagc     420
caaaacaaca gccccatcgg tctatccact ggccctgtg tgtggagata caactggctc     480
```

```
ctcggtgact ctaggatgcc tggtcaag                                   508

<210> SEQ ID NO 2
<211> LENGTH: 444
<212> TYPE: DNA
<213> ORGANISM: Mus musculus

<400> SEQUENCE: 2
caccatggat tttcaggtgc agattttcag cttcctgcta atcagtgcct cagtcataat    60
gtccagagga caaattgttc tcacccagtc tccagcaatc atgtctgcat ctctagggga   120
acgggtcacc atgacctgca ctgccacctc aagtgtaagt tccagttact tgcactggta   180
ccagcagaag ccaggatcct cccccaaact ctggatttat agcacatcca acctggcttc   240
tggagtccca gctcgcttca gtggcagtgg gtctgggacc tcttactctc tcacaatcag   300
cagcatggag gctgaagatg ctgccactta ttactgccac cagtatcatc gttccccacc   360
gtggacgttc ggtggaggca ccaagctgga aatcaaacgg gctgatgctg caccaactgt   420
atccatctcc ccccatccag tgta                                         444

<210> SEQ ID NO 3
<211> LENGTH: 30
<212> TYPE: DNA
<213> ORGANISM: Mus musculus

<400> SEQUENCE: 3
gggttttcac tgagcacttc tggtatgggt                                    30

<210> SEQ ID NO 4
<211> LENGTH: 21
<212> TYPE: DNA
<213> ORGANISM: Mus musculus

<400> SEQUENCE: 4
atttactggg atgatgacaa g                                             21

<210> SEQ ID NO 5
<211> LENGTH: 33
<212> TYPE: DNA
<213> ORGANISM: Mus musculus

<400> SEQUENCE: 5
gctcgaagag atgggacacg ggggtttgac tac                                33

<210> SEQ ID NO 6
<211> LENGTH: 21
<212> TYPE: DNA
<213> ORGANISM: Mus musculus

<400> SEQUENCE: 6
tcaagtgtaa gttccagtta c                                             21

<210> SEQ ID NO 7
<211> LENGTH: 30
<212> TYPE: DNA
<213> ORGANISM: Mus musculus

<400> SEQUENCE: 7
caccagtatc atcgttcccc accgtggacg                                    30

<210> SEQ ID NO 8
<211> LENGTH: 21
```

```
<212> TYPE: PRT
<213> ORGANISM: Epstein-Barr virus

<400> SEQUENCE: 8

Cys Val Gly Lys Asn Asp Lys Glu Glu Ala His Gly Val Tyr Val Ser
1               5                   10                  15

Gly Tyr Leu Ser Gln
            20

<210> SEQ ID NO 9
<211> LENGTH: 17
<212> TYPE: PRT
<213> ORGANISM: Epstein-Barr virus

<400> SEQUENCE: 9

Cys Arg Met Lys Leu Gly Glu Thr Glu Val Thr Lys Gln Glu His Leu
1               5                   10                  15

Ser

<210> SEQ ID NO 10
<211> LENGTH: 14
<212> TYPE: PRT
<213> ORGANISM: Epstein-Barr virus

<400> SEQUENCE: 10

Glu Arg Val Thr Leu Thr Ser Tyr Trp Arg Arg Val Ser Leu
1               5                   10

<210> SEQ ID NO 11
<211> LENGTH: 8
<212> TYPE: PRT
<213> ORGANISM: Epstein-Barr virus

<400> SEQUENCE: 11

Arg Val Thr Leu Thr Ser Tyr Trp
1               5

<210> SEQ ID NO 12
<211> LENGTH: 8
<212> TYPE: PRT
<213> ORGANISM: Epstein-Barr virus

<400> SEQUENCE: 12

Thr Ser Tyr Trp Arg Arg Val Ser
1               5

<210> SEQ ID NO 13
<211> LENGTH: 221
<212> TYPE: PRT
<213> ORGANISM: Epstein-Barr virus

<400> SEQUENCE: 13

Met Ala Arg Phe Ile Ala Gln Leu Leu Leu Ala Ser Cys Val Ala
1               5                   10                  15

Ala Gly Gln Ala Val Thr Ala Phe Leu Gly Glu Arg Val Thr Leu Thr
            20                  25                  30

Ser Tyr Trp Arg Arg Val Ser Leu Gly Pro Glu Ile Glu Val Ser Trp
        35                  40                  45

Phe Lys Leu Gly Pro Gly Glu Glu Gln Val Leu Ile Gly Arg Met His
    50                  55                  60

His Asp Val Ile Phe Ile Glu Trp Pro Phe Arg Gly Phe Phe Asp Ile
65                  70                  75                  80
```

```
His Arg Ser Ala Asn Thr Phe Phe Leu Val Val Thr Ala Ala Asn Ile
                85                  90                  95

Ser His Asp Gly Asn Tyr Leu Cys Arg Met Lys Leu Gly Glu Thr Glu
            100                 105                 110

Val Thr Lys Gln Glu His Leu Ser Val Val Lys Pro Leu Thr Leu Ser
        115                 120                 125

Val His Ser Glu Arg Ser Gln Phe Pro Asp Phe Ser Val Leu Thr Val
    130                 135                 140

Thr Cys Thr Val Asn Ala Phe Pro His Pro His Val Gln Trp Leu Met
145                 150                 155                 160

Pro Glu Gly Val Glu Pro Ala Pro Thr Ala Ala Asn Gly Gly Val Met
                165                 170                 175

Lys Glu Lys Asp Gly Ser Leu Ser Val Ala Val Asp Leu Ser Leu Pro
            180                 185                 190

Lys Pro Trp His Leu Pro Val Thr Cys Val Gly Lys Asn Asp Lys Glu
        195                 200                 205

Glu Ala His Gly Val Tyr Val Ser Gly Tyr Leu Ser Gln
    210                 215                 220

<210> SEQ ID NO 14
<211> LENGTH: 11
<212> TYPE: PRT
<213> ORGANISM: Epstein-Barr virus

<400> SEQUENCE: 14

Arg Val Thr Leu Thr Ser Tyr Trp Arg Arg Val
1               5                   10

<210> SEQ ID NO 15
<211> LENGTH: 7
<212> TYPE: PRT
<213> ORGANISM: Epstein-Barr virus

<400> SEQUENCE: 15

Thr Ser Tyr Trp Arg Arg Val
1               5

<210> SEQ ID NO 16
<211> LENGTH: 136
<212> TYPE: DNA
<213> ORGANISM: Mus musculus

<400> SEQUENCE: 16
caccatgggc aggcttacat cctcattcct gctgctgatt gtccctgcat atgtcctttc      60
ccaggttact ctgaaagagt ctggccctgg gatattgcag ccctcccaga ccctcagtct     120
gacttgttct ttctct                                                    136

<210> SEQ ID NO 17
<211> LENGTH: 51
<212> TYPE: DNA
<213> ORGANISM: Mus musculus

<400> SEQUENCE: 17
gtgagctgga ttcgtcagcc ttcaggaaag ggtctggagt ggctggcaca c               51

<210> SEQ ID NO 18
<211> LENGTH: 114
<212> TYPE: DNA
<213> ORGANISM: Mus musculus
```

```
<400> SEQUENCE: 18
cgctataacc catccctgaa gagccggctc acaatctcca aggatacctc cagaaaccag      60
gtattcctca agatcaccag tgtggacact gcagatactg ccacatacta ctgt           114

<210> SEQ ID NO 19
<211> LENGTH: 29
<212> TYPE: DNA
<213> ORGANISM: Mus musculus

<400> SEQUENCE: 19
tggggccaag gcaccactct cacagtctc                                        29

<210> SEQ ID NO 20
<211> LENGTH: 94
<212> TYPE: DNA
<213> ORGANISM: Mus musculus

<400> SEQUENCE: 20
ctcagccaaa acaacagccc catcggtcta tccactggcc cctgtgtgtg gagatacaac      60
tggctcctcg gtgactctag gatgcctggt caag                                  94

<210> SEQ ID NO 21
<211> LENGTH: 148
<212> TYPE: DNA
<213> ORGANISM: Mus musculus

<400> SEQUENCE: 21
caccatggat tttcaggtgc agattttcag cttcctgcta atcagtgcct cagtcataat      60
gtccagagga caaattgttc tcacccagtc tccagcaatc atgtctgcat ctctagggga     120
acgggtcacc atgacctgca ctgccacc                                        148

<210> SEQ ID NO 22
<211> LENGTH: 51
<212> TYPE: DNA
<213> ORGANISM: Mus musculus

<400> SEQUENCE: 22
ttgcactggt accagcagaa gccaggatcc tcccccaaac tctggattta t              51

<210> SEQ ID NO 23
<211> LENGTH: 108
<212> TYPE: DNA
<213> ORGANISM: Mus musculus

<400> SEQUENCE: 23
aacctggctt ctggagtccc agctcgcttc agtggcagtg ggtctgggac ctcttactct      60
ctcacaatca gcagcatgga ggctgaagat gctgccactt attactgc                  108

<210> SEQ ID NO 24
<211> LENGTH: 30
<212> TYPE: DNA
<213> ORGANISM: Mus musculus

<400> SEQUENCE: 24
ttcggtggag gcaccaagct ggaaatcaaa                                       30

<210> SEQ ID NO 25
<211> LENGTH: 47
<212> TYPE: DNA
```

-continued

```
<213> ORGANISM: Mus musculus

<400> SEQUENCE: 25
cgggctgatg ctgcaccaac tgtatccatc tcccccatc cagtgta                    47

<210> SEQ ID NO 26
<211> LENGTH: 9
<212> TYPE: DNA
<213> ORGANISM: Mus musculus

<400> SEQUENCE: 26 agcacatcc                                                              9
```

ANTI-BARF1 MONOCLONAL ANTIBODY

CROSS REFERENCE TO RELATED APPLICATIONS

This application is a U.S. National Phase of PCT Patent Application No. PCT/EP2016/076691, filed Nov. 4, 2016, which claims priority to Italian Patent Application No. 102015000069010, filed Nov. 4, 2015, each of which is incorporated herein by reference in its entirety.

REFERENCE TO SEQUENCE LISTING SUBMITTED ELECTRONICALLY

The content of the electronically submitted sequence listing in ASCII text file (Name: 5713_0025_amended_sequence_listing.txt; Size: 7,936 bytes; and Date of Creation: Aug. 12, 2020) filed on Aug. 17, 2020 is herein incorporated by reference in its entirety.

DESCRIPTION

The present invention finds application in the field of medicine and, in particular, in the treatment and diagnosis of tumors.

Epstein-Barr virus (EBV) is a γ-herpes virus associated with human tumors, such as nasopharyngeal carcinoma (NPC), Hodgkin's lymphoma (HL), Burkitt's lymphoma, some T-cell and NK-cell lymphomas, Diffuse Large B-cell lymphomas, post-transplant EBV+ lymphoproliferations, and gastric carcinoma (GC).

The virus usually infects about 95% of the population asymptomatically. Occasionally, the virus can reactivate and be present in infectious form in saliva. In addition to latent genes, whose differential expression characterizes the various forms of latency encountered in tumors, two non-coding and non-polyadenylated RNAs, i.e. EBER1 and EBER2, are expressed in all forms of viral latency.

Recent studies have shown that BamH1-A rightward frame-1 (BARF1) is a protein expressed in latently-infected tumor cells of EBV-associated NPCs and in gastric carcinoma.

BARF1 shares limited homology with the receptor of the human colony-stimulating factor 1 (the oncogene FMS) and shows oncogenic activity when expressed in fibroblasts of rodents and in primary epithelial cells of monkeys.

The BARF1 gene is located between the nucleotide positions 165.449-166.189 of the EBV genome of the B95.8 strain, and encodes a protein of 221 amino acids. The gene encodes for a transmembrane protein expressed on the surface of EBV-infected cells, which may be present also in a secreted form.

The immortalizing effects of BARF1 on epithelial primary cells from primates (Wei et al. 1997) and the malignant transformation in rodent fibroblasts (Wei and Ooka 1989) have already been described.

Interestingly, the extracellular domain of BARF1 can be cleaved and released from the cells, and can act as a growth factor in vivo; it can inhibit the secretion of α-interferon from mononuclear cells and has mitogenic activity in vivo.

The biological effects of the intracellular and secreted forms of the protein still have to be fully elucidated, and the identification of the receptor for the secreted form of BARF1 seems to be of great importance for understanding the functions of BARF1 in vivo.

Given the important pathogenetic role of BARF1 in the development of EBV-associated neoplasias, and considering that this protein may represent a valid therapeutic target for these tumors, the development of a BARF1-specific monoclonal antibody (mAb) can represent a strategy of considerable therapeutic relevance for a more effective control of these neoplasias.

SUMMARY OF THE INVENTION

The present invention describes the development and isolation of a BARF1-specific monoclonal antibody (mAb) as well as the in vitro characterization thereof and the description of in vivo induced therapeutic effects in animal models.

The mAb has been shown to be effective in complement activation assays (Complement-Dependent Cytotoxicity, CDC) and in the induction of Antibody-Dependent Cell-mediated Cytotoxicity (ADCC) in vitro, essential prerequisites for an efficient therapeutic activity in vivo.

Moreover, the in vivo biodistribution analysis conducted using the anti-BARF1 antibody conjugated with a fluorochrome has shown a selective antibody localization at the level of the EBV-positive tumor mass.

The mAb has been used for in vivo passive immunotherapy experiments by injection into SCID mice, previously transplanted with different types of EBV-positive or negative cells, and has been shown to be able to selectively slow tumor growth of EBV-positive, BARF1-expressing tumor cells.

Finally, using the in vivo imaging of luciferase-transduced tumor cells, it was possible to monitor in vivo the activity of mAb over time and confirm the therapeutic effect of the treatment in tumor-bearing mice.

Overall, these data indicate that BARF1 is a new EBV-specific targetable antigen, and that the use of anti-BARF1 monoclonal antibodies can be a powerful tool for the detection and treatment of tumors related to the virus.

OBJECT OF THE INVENTION

In a first object, the present invention provides the sequences of the complementarity-determining regions (CDR) of the variable domains of the heavy chain and the light chain of the anti-BARF1 monoclonal antibody, as well as of the entire variable domains of the heavy and light chain.

In particular, sequences CDR1, CDR2 and CDR3 of the heavy chains correspond to sequences SEQ ID NO:3, 4 and 5, respectively, while the CDR1, CDR2 and CDR3 of the light chain correspond to sequence SEQ ID NO:6, sequence AGCACATCC (SEQ ID NO: 26) and sequence SEQ ID NO:7, respectively.

With regard to the variable domain of the heavy chain, this is encoded by the sequence corresponding to SEQ ID NO:1, while that of the light chain corresponds to SEQ ID NO:2.

Each sequence represents a further object of the invention.

The present invention therefore describes an antibody derived from the expression of immunoglobulin genes composed of the sequences described above.

According to the invention, the antibody may be a whole immunoglobulin or an immunoglobulin fragment comprising at least one variable domain of the heavy chain and one variable domain of the light chain.

Said fragment is preferably a Fab fragment, a F(ab')2 fragment, a single-chain Fv fragment (single chain Fragment variable, scFv) or derivatives thereof (diabody, triabody, etc.).

In a particular aspect, this single-chain Fv fragment is linked to lymphoid signal transduction domains in the format of a Chimeric Antigen Receptor (CAR).

Even more particularly, said domains may comprise: CD28, CD3ζ, CD137, OX-40.

The antibody of the invention or a fragment thereof may be either humanized or murine.

The antibody is also described for medical use and, in particular, is described herein in the context of treatment and diagnosis of tumors related to Epstein-Barr virus infection or otherwise expressing epitopes homologous to that of BARF1 recognized by said antibody.

In particular, in the treatment and diagnosis of human cancers, such as nasopharyngeal carcinoma (NPC), Hodgkin's lymphoma (HL), Burkitt's lymphoma, non-Hodgkin EBV+ lymphomas, T-cell and NK-cell lymphomas, Diffuse large B-cell lymphomas, post-transplant EBV+ lymphoproliferations, and gastric carcinoma (GC).

The antibody is also described for use in the production of Chimeric Antigen Receptor and for the transduction of lymphoid cells for adoptive immunotherapy.

A further object of the invention provides a viral antigen peptide (hereinafter indicated with 08/08) having a sequence corresponding to SEQ ID NO:10 or to SEQ ID NO:14 and an octamer having a sequence corresponding to SEQ ID NO:11 or SEQ ID NO:12, which is preferably that having SEQ ID NO:11.

Such peptides and such an octamer, together with their cellular homologues such as immunogenic epitopes, are described herein for medical use, in particular in immunization and active vaccination protocols.

For this purpose, a pharmaceutical preparation is described herein comprising the antibody or one or more of the peptides of the present invention, together with one or more pharmaceutically acceptable excipients.

The present invention describes a method for the diagnosis or treatment of tumors including the step of administering a pharmacologically effective amount of the antibody described in the present patent application to a patient.

According to a further aspect, the invention describes a method for the diagnosis or treatment of tumors comprising the step of administering a pharmacologically effective amount of one of the viral antigen peptides described above to a patient.

In particular, such peptides are those having a sequence that corresponds to SEQ ID NO:10 or SEQ ID NO:11 or SEQ ID NO:12 or SEQ ID NO:14; preferably such peptide corresponds to SEQ ID NO:11.

The present invention further describes a method for the treatment or diagnosis of tumors comprising the step of administering a pharmacologically effective amount of a pharmaceutical preparation comprising the antibody or one of the viral antigenic peptides described above to a patient.

According to a particular aspect, the method for the treatment or diagnosis of the present invention relates to Epstein-Barr virus-related tumors.

In another particular aspect, the tumor expresses epitopes homologous to that of BARF1 recognized by said antibody.

According to a further aspect, the invention describes a method for the immunization or vaccination of a patient, possibly for the active vaccination, comprising the step of administering a pharmaceutically effective amount of a viral antigen peptide as described above to said patient.

In particular, such a peptide is characterized by a sequence that corresponds to SEQ ID NO:10 or SEQ ID NO:11 or SEQ ID NO:12 or SEQ ID NO:14; preferably such peptide corresponds to SEQ ID NO:11.

According to an alternative aspect, the present invention describes a method for the immunization or vaccination of a patient comprising the step of administering a pharmaceutically effective amount of a pharmaceutical preparation comprising the antibody or one of the peptides described above to said patient.

BRIEF DESCRIPTION OF THE FIGURES

FIGS. 1a-1d: a) Amino acid sequence of the BARF1 protein corresponding to SEQ ID NO:13. b) Dot Blot. The peptides used for the immunization and the peptides derived from peptide 08/08' were bound to a PVDF membrane and labeled with anti-BARF1 antibody. Positivity is only present for peptides 08/08' and 08/08-1, which therefore represent the minimum epitope of the selected antigen. Peptide sequences 05/08 (SEQ ID NO: 8), 06/08 (SEQ ID NO: 9), 08/08' (SEQ ID NO: 14), 08/08-1 (SEQ ID NO: 11), and 08/08-2 (SEQ ID NO: 15) are shown. c) Fluorescence and mean fluorescence intensity (MFI) percentages of three BARF1-positive (GRANTA-519, C-666, BL-41 B95.8) and two BARF1-negative (RAJI and BL-41) cell lines, as a result of the flow cytometry analysis. d) Flow cytometry. MKN-45 cells were transduced with BARF1-encoding plasmid and labeled with anti-BARF1 mAb. The transduced cell line showed a high positive signal.

FIGS. 4a-4c: a) Growth kinetics of tumors induced by s.c. inoculation of C-666 cells ($5\times10^6$) in SCID mice. Five mice were not treated, while 9 mice received a total of 1 mg of anti-BARF1 antibody. Statistical analysis (Wilcoxon test) showed that the reduction of tumor growth achieved by the administration of anti-BARF1 mAb is statistically significant at days 24, 26, and 28 (p=0.0028, p=0.002 and p=0.0026, respectively). b) Bioluminescence analysis of mice injected subcutaneously on day 0 with $5\times10^6$ C-666-LUX cells. The images refer to day 14 and 49 of the control group (ctrl, not treated) and of the treatment group (anti-BARF1 mAb). Values are expressed as radiance (p/sec/cm$^2$/sr). c) Statistical analysis of the radiance of mice injected s.c. on day 0 with $5\times10^6$ C-666-LUX cells. Control group was not treated, while the treatment group received anti-BARF1 mAb (1 mg). At day 49, the average brightness of the treated group is significantly lower compared to the control (p<0.001).

Figure 2A:
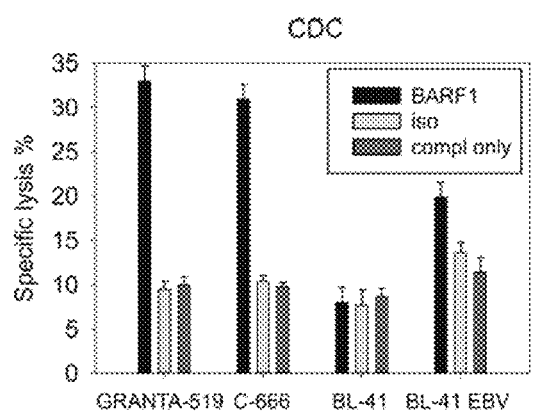
FIGS. 2a-2b: a) CDC (complement-dependent cytotoxicity). Percentage of specific lysis of EBV-positive (GRANTA-519, C-666 and BL-41 B95.8) and EBV-negative (BL-41) cell lines after exposure to different concentrations of anti-BARF1 mAb followed by the complement. All EBV-positive cell lines were lysed, although to a different extent, while the EBV-negative cell line was not lysed. For each experimental condition, the isotype control was used as a negative control. b) ADCC (Antibody-Dependent Cell-mediated Cytotoxicity). Specific lysis of EBV-positive (GRANTA-519 and C-666) and EBV-negative (BL-41) cell lines after exposure to the anti-BARF1 mAb followed by human effector cells (PBMCs). All EBV-positive cell lines were lysed, although to a different extent, while the EBV-negative cell line was not lysed. For each experimental condition, the isotype control and the presence of effector cells in the absence of immunoglobulins (only PBMCs) were used as negative controls.

FIGS. 5a-5d: a) Growth kinetics of tumors induced by subcutaneous inoculation of GRANTA-519 cells (5×10$^6$) in SCID mice. Nine mice were not treated, while 13 mice received a total of 1 mg of anti-BARF1 antibody. Statistical analysis (Wilcoxon test) showed that the reduction of tumor growth achieved by the administration of anti-BARF1 mAb is statistically significant at day 21 (p<0.001). b) Survival analysis of SCID mice inoculated intravenously with GRANTA-519 cells. Kaplan-Meier test showed a statistically significant improvement in the survival of the treated group (p=0.002). c) Bioluminescence analysis of mice injected intravenously on day 0 with 3×10$^6$ GRANTA-519-LUX cells. The images refer to day 14 and 21 of the control group (not treated) and of the treatment group (anti-BARF1 mAb). The presence of signals in the lymph node area can be observed. Values are expressed as radiance (p/sec/cm$^2$/sr). d) Statistical analysis of the radiance of mice injected i.v. on day 0 with 3×10$^6$ GRANTA-519-LUX cells. At day 21, the average radiance of the treated group was significantly lower compared to the control group (p<0.05).

DETAILED DESCRIPTION OF THE INVENTION

The following sequences were identified:
VH Hybridoma 3D4

```
SEQ ID NO: 1:
CACCATGGGCAGGCTTACATCCTCATTCCTGCTGCTGATTGTCCCTGCAT
ATGTCCTTTCCCAGGTTACTCTGAAAGAGTCTGGCCCTGGGATATTGCAG
CCCTCCCAGACCCTCAGTCTGACTTGTTCTTTCTCTGGGTTTTCACTGAG
CACTTCTGGTATGGGTGTGAGCTGGATTCGTCAGCCTTCAGGAAAGGGTC
TGGAGTGGCTGGCACACATTTACTGGGATGATGACAAGCGCTATAACCCA
TCCCTGAAGAGCCGGCTCACAATCTCCAAGGATACCTCCAGAAACCAGGT
ATTCCTCAAGATCACCAGTGTGGACACTGCAGATACTGCCACATACTACT
GTGCTCGAAGAGATGGGACACGGGGGTTTGACTACTGGGGCCAAGGCACC
ACTCTCACAGTCTCCTCAGCCAAAACAACAGCCCCATCGGTCTATCCACT
GGCCCCTGTGTGTGGAGATACAACTGGCTCCTCGGTGACTCTAGGATGCC
TGGTCAAG
``` wherein

| | | |
|---|---|---|
| CACCATGGGCAGGCTTACATCCTCAT TCCTGCTGCTGATTGTCCCTGCATAT GTCCTTTCCCAGGTTACTCTGAAAGA GTCTGGCCCTGGGATATTGCAGCCCT CCCAGACCCTCAGTCTGACTTGTTCT TTCTCT | FR1 | SEQ ID NO: 16 |
| GGGTTTTCACTGAGCACTTCTGGTAT GGGT | CDR1 | SEQ ID NO: 3 |
| GTGAGCTGGATTCGTCAGCCTTCAGG AAAGGGTCTGGAGTGGCTGGCACAC | FR2 | SEQ ID NO: 17 |
| ATTTACTGGGATGATGACAAG | CDR2 | SEQ ID NO: 4 |
| CGCTATAACCCATCCCTGAAGAGCCG GCTCACAATCTCCAAGGATACCTCCA | FR3 | SEQ ID NO: 18 |
| GAAACCAGGTATTCCTCAAGATCACC AGTGTGGACACTGCAGATACTGCCAC ATACTACTGT | | |
| GCTCGAAGAGATGGGACACGGGGGTT TGACTAC | CDR3 | SEQ ID NO: 5 |
| TGGGGCCAAGGCACCACTCTCACAGT CTC | FR4 | SEQ ID NO: 19 |
| CTCAGCCAAAACAACAGCCCCATCGG TCTATCCACTGGCCCCTGTGTGTGGA GATACAACTGGCTCCTCGGTGACTCT AGGATGCCTGGTCAAG | CH1 | SEQ ID NO: 20 |

VK Hybridoma 3D4

```
SEQ ID NO: 2:
VK hybridoma 3D4
CACCATGGATTTTCAGGTGCAGATTTTCAGCTTCCTGCTAATCAGTGCCT
CAGTCATAATGTCCAGAGGACAAATTGTTCTCACCCAGTCTCCAGCAATC
ATGTCTGCATCTCTAGGGGAACGGGTCACCATGACCTGCACTGCCACCTC
AAGTGTAAGTTCCAGTTACTTGCACTGGTACCAGCAGAAGCCAGGATCCT
CCCCCAAACTCTGGATTTATAGCACATCCAACCTGGCTTCTGGAGTCCCA
GCTCGCTTCAGTGGCAGTGGGTCTGGGACCTCTTACTCTCTCACAATCAG
CAGCATGGAGGCTGAAGATGCTGCCACTTATTACTGCCACCAGTATCATC
GTTCCCCACCGTGGACGTTCGGTGGAGGCACCAAGCTGGAAATCAAACGG
GCTGATGCTGCACCAACTGTATCCATCTCCCCCCATCCAGTGTA
``` wherein:

| | | |
|---|---|---|
| CACCATGGATTTTCAGGTGCAGATTT TCAGCTTCCTGCTAATCAGTGCCTCA GTCATAATGTCCAGAGGACAAATTGT TCTCACCCAGTCTCCAGCAATCATGT CTGCATCTCTAGGGGAACGGGTCACC ATGACCTGCACTGCCACC | FR1 | SEQ ID NO: 21 |
| TCAAGTGTAAGTTCCAGTTAC | CDR1 | SEQ ID NO: 6 |
| TTGCACTGGTACCAGCAGAAGCCAGG ATCCTCCCCCAAACTCTGGATTTAT | FR2 | SEQ ID NO: 22 |
| AGCACATCC | CDR2 | SEQ ID NO: 26 |
| AACCTGGCTTCTGGAGTCCCAGCTCG CTTCAGTGGCAGTGGGTCTGGGACCT CTTACTCTCTCACAATCAGCAGCATG GAGGCTGAAGATGCTGCCACTTATTA CTGC | FR3 | SEQ ID NO: 23 |
| CACCAGTATCATCGTTCCCCACCGTG GACG | CDR3 | SEQ ID NO: 7 |
| TTCGGTGGAGGCACCAAGCTGGAAAT CAAA | FR4 | SEQ ID NO: 24 |
| CGGGCTGATGCTGCACCAACTGTATC CATCTCCCCCCATCCAGTGTA | CL | SEQ ID NO: 25 |

Materials and Methods
Cell Lines:
The following human cell lines were used: GRANTA-519 (mantle B-cell lymphoma, EBV+, BARF1+), C-666 (NPC, EBV+, BARF1+), BL-41 (Burkitt's lymphoma, EBV−), BL-41 B95.8 (the same cell line infected with EBV), Raji (lymphoblastic-like cell line B, EBV+, but BARF1−), and MKN-45 (gastric carcinoma, EBV−).

B95.8 is a monkey cell line used for the generation of EBV virions. All cell lines, except for MKN-45, were cultured in RPMI 1640 medium (Euroclone), supplemented with 10% heat-inactivated fetal calf serum (FBS, Gibco), 10 mM Hepes, 1 mM Na pyruvate, 2 mM Ultraglutamine (all from Lonza BioWhittaker), and 1% antibiotic/antifungal (Gibco), hereinafter referred to as complete RPMI medium.

MKN-45 was grown in DMEM supplemented with the same additives, referred to as complete DMEM medium.

The NS0 cell line is a mouse myeloma line used for the generation of hybridomas. NS0 cells are cultured in DMEM supplemented with 10% heat-inactivated FBS, 10 mM Hepes, $5 \times 10^{-3}$ mM β-mercaptoethanol, 2 mM Ultraglutamine, 1% antibiotic/antifungal.

Antibody Production

The BARF1 sequence was analyzed using bioinformatics tools.

Three major epitopes were identified:

```
05/08₂₀₁₋₂₂₁    CVGKNDKEEAHGVYVSGYLSQ    SEQ ID NO: 8

06/08₁₀₄₋₁₂₀    CRMKLGETEVTKQEHLS        SEQ ID NO: 9

08/08₂₇₋₄₀      ERVTLTSYWRRVSL           SEQ ID NO: 10

08/08'₂₈₋₃₈     RVTLTSYWRRV              SEQ ID NO: 14
```

The peptides were conjugated to KLH (Keyhole Limpet Hemocyanin) using the Imject Maleimide Activated mcKLH kit (Thermo Scientific) and used for the vaccination of mice.

The anti-BARF1 hybridoma was derived from the fusion of murine NS0 myeloma cells with spleen cells of a BALB/c mouse which had been immunized once subcutaneously with 100 μg of each of the KLH-conjugated peptides in Complete Freund's Adjuvant (CFA) and then twice with 100 μg of each of the KLH-conjugated peptides in Incomplete Freund's Adjuvant (IFA).

When necessary, additional vaccinations were carried out in IFA.

Spleen cells from immunized mice were collected and fused with NS0 myeloma cells using polyethylene glycol (PEG) according to standard procedures.

After fusion, cells were seeded in 96-well plates and hybridomas were selected in a medium containing hypoxanthine-aminopterin-thymidine (HAT).

Hybridoma lines capable of growing in the selection medium were screened for anti-BARF1 reactivity by enzyme immunoassay (ELISA) and flow cytometry.

The ELISA test was performed as follows: 96-well plates were incubated overnight at 4° C. with 100 μL/well of the specific peptide (10 μg/mL); after blocking with 1% BSA for 2 hours at 37° C., they were incubated for 1 hour at 37° C. with 100 μL of hybridoma supernatant and, after repeated washing, for 1 hour with HRP-conjugated anti-mouse goat antibody (GE Healthcare).

After signal development using OPD (Sigma-Aldrich), the reaction was quenched with 50 μL of 3 N hydrochloric acid and the absorbance was read at 450 nm with a Victor Multilabel X3 plate reader (Perkin Elmer). For flow cytometry, GRANTA-519 cells were labeled with the clone supernatant, then a secondary FITC anti-mouse antibody was added (Dako) and the cells were analyzed using FACSCalibur (BD).

Only the clones that gave a positive signal as evaluated by flow cytometry were used for the subsequent experiments.

Antibody specificity was evaluated by Dot Blot.

Briefly, 8-mer peptides overlapping of 4-amino acids derived from the original peptides $08/08_{27\text{-}40}$ and $08/08'_{28\text{-}38}$, were synthesized: in fact, the mAb used for all experiments is derived from a mouse immunized with this latter peptide.

The 8-mer overlapping peptides and the original $08/08_{27\text{-}40}$, $08/08'_{28\text{-}38}$, $05/08_{201\text{-}221}$ and $06/08_{104\text{-}120}$ peptides were transferred on a PVDF membrane (about 10 μg/spot, Millipore).

After blocking with PBS/10% Tween/3% BSA, plates were incubated with anti-BARF1 mAb, then with an HRP-conjugated anti-mouse goat Ig, and finally the signal was detected using the ECL Plus Western Blotting Substrate (Pierce).

Chemiluminescence was evaluated using the XRS Chemidoc instrument and QuantityOne software (vers. 4.6) (both from BioRad).

In Vitro Assays

Labels

EBV-negative (BL-41), EBV-positive but BARF1-negative (Raji) and EBV-positive and BARF1-positive (GRANTA-519, C-666 and BL-41 B95.8) cell lines were labeled with 1 μg of anti-BARF1 mAb for 15 minutes on ice and then with a secondary anti-mouse FITC IgG.

In order to specifically identify BARF1, a BARF1-transduced cell line was generated.

The BARF1 plasmid was kindly provided by the laboratory of Dottor Dolcetti and used to transfect Phoenix cells as described above.

BARF1-retroviral (BARF1-RV) particles were stored at −80° C.

An EBV-negative cell line, MKN-45, was plated ($4 \times 10^6$) with 2 mL BARF1-RV in a 6-well plate in the presence of polybrene (8 mg/mL).

After centrifugation (45 min. at 1800 rpm), the cells were incubated at 32° C. for 2 hours, and the medium was replaced with 2 mL of fresh medium containing BARF1-RV and polybrene.

After further centrifugation, the MKN-45 cells were incubated at 32° C. for 4 hours, then the medium was replaced with fresh complete DMEM medium and left overnight at 37° C.

The next day, complete DMEM medium was replaced with 4 ml of BARF1-RV with polybrene and centrifuged; after incubation at 32° C. for 5 hours, the medium containing the viral particles was replaced with complete DMEM and incubated at 37° C.

The selection with G418 (250 μg/mL, Sigma-Aldrich) started the next day.

After one week in culture in the presence of G418, BARF1-transduced cells and wild-type cells were analyzed for the presence of BARF1 mRNA by RT-PCR.

The cells were also analyzed by flow cytometry using an anti-BARF1 antibody.

Complement-Dependent Cytotoxicity (CDC)

Target cells ($6 \times 10^5$ GRANTA-519 cells, C-666, and Raji) were loaded with 100 μCi $Na_2^{51}CrO_4$ (Perkin-Elmer) for 1 hour and 30 minutes at 37° C.

The cells were then seeded at $2 \times 10^3$ cells/well in triplicate and labeled with about 1 μg anti-BARF1 mAb.

Then, cells were resuspended in 200 μL of RPMI containing 25% human serum (non-heat inactivated, thereby keeping all the proteins of the complement still active; Lonza), for 1 hour at 37° C.

Negative (or spontaneous release) controls were not labeled with the mAb, while 100 μL of 5% Triton (Sigma-Aldrich) were added for the positive control (maximum release).

After incubation, 100 μL of supernatant were evaluated for radioactivity using a γ-ray counter (Cobra Gamma Counting System, Packard Instrument Company).

The cytotoxicity index was evaluated as follows:

$$C.I. = 100 \times \frac{\% \ test - \% \ spont}{100\% - \% \ spont}$$

where:
% test is the percentage of cytotoxicity obtained with mAb plus complement,
% spont is the percentage of cytotoxicity of the complement alone.

Antibody-Dependent Cell-Mediated Cytotoxicity (ADCC)

ADCC was performed using the calcein-AM protocol (Invitrogen).

In brief, $1 \times 10^6$ target cells were resuspended in 1 mL of Hank's balanced salt solution supplemented with 5% FBS (HBSS-FBS, 5.4 mM KCl, 0.3 mM $Na_2HPO_4$, 0.4 mM $KH_2PO_4$, 0.2 mM $NaHCO_3$, 0.5 mM $MgCl_2$, 0.4 mM $MgSO_4$, 137 mM NaCl, all from Sigma-Aldrich) and labeled with 7.5 μL calcein-AM 1 mg/mL for 30 minutes at 37° C.

Cells were then labeled with anti-BARF1 mAb at a concentration of 20 μg/mL, 10 μg/mL and 5 μg/mL; negative controls were carried out with HBSS-FBS only.

As positive control, target cells were lysed with 5% Triton.

After seeding, cells were added to effector cells: PBMCs just thawed from healthy donors were seeded at different effector:target ratios (300:1, 150:1 and 75:1) for 4 hours at 37° C., then 100 μL of supernatant were collected and seeded on an opaque 96-well plate (Nunc).

After 15 minutes at RT, the plate was read at 485 nm using the Victor X3 Multilabel Reader Plate instrument.

The percentage of lysis (% Lys) was calculated as follows:

$$\% \ lysis = 100 \times \frac{test - spont}{max - spont}$$

where:
test is the experimental value,
spont is the value of target cells not treated, and
max is the positive control value.

In Vivo Assays
Biodistribution

In order to study the biodistribution of antibodies, the monoclonal anti-BARF1 was conjugated with Alexa 680, using the SAIVI Rapid Antibody Labeling Kit (Invitrogen) and following the manufacturer's directions.

SCID mice were injected subcutaneously with an EBV-negative cell line (such as MKN-45) on one side and with an EBV-positive cell line (such as BARF1-MKN-45, C-666 or SNU-719) on the other side.

As soon as both tumors became palpable, 100 μg of Alexa-680 anti-BARF1 antibody were injected into the caudal vein of the anesthetized animal and the fluorescence signal was analyzed every 24 hours by using the eXplore Optix device (GE Healthcare).

The fluorescence intensity detected on the tumor masses was compared and the trend analyzed with the ANOVA statistical test for repeated measurements.

Therapy

Mice were kept in plastic cages at a constant temperature and with a balanced diet in an SPF (Specific Pathogen Free) animal house.

Procedures involving animals and their care were conducted in accordance with institutional guidelines in compliance with national laws (Legislative Decree No. 116/92) and Ceasa (University of Padua, Ethics Committee for animal experimentation).

All in vivo tumor growth experiments were conducted in accordance with the guidelines of the United Kingdom Co-ordinating Committee on Cancer Research (UKCCCR) (Cancer Metastasis 1989 "UKCCCR guidelines for the welfare of animals in experimental neoplasia").

SCID and $RAG^{-/-}\gamma$-$chain^{-/-}$ mice aged six to eight weeks were injected s.c. with $5 \times 10^6$ GRANTA-519 or C-666 cells.

Mice were then divided into untreated and treated groups, respectively, receiving 1 mL of PBS or 1 mg of monoclonal anti-BARF1 (5 i.p. injections of 0.2 mL each, one every two days).

Tumor mass growth was evaluated every two days by measuring the maximum and minimum diameter, and was calculated by applying the formula:

$$Tmass = \frac{d^2 \times D}{2}$$

where d is the minimum diameter and D is the maximum diameter.

In order to better evaluate the tumor growth kinetics, an in vivo imaging approach based on luciferase was used.

For this purpose, tumor cell lines were transduced with the luciferase enzyme.

Briefly, luciferase-encoding lentiviral particles (LUX-LV) were produced in 293T cells by transient cotransfection of the vector (pHR'tripCMV-luc2-IRES-tNGFR-SIN), the envelope plasmid (HCMV-G) and the packaging plasmid (p8.74), following a protocol already published.

The virus was harvested 48 and 72 hours after transfection and concentrated by ultracentrifugation.

$5 \times 10^5$ GRANTA-519 and C-666 cells were harvested and resuspended in 1 mL of complete RPMI medium with concentrated (3- to 5-fold) LV-LUX.

Cells were incubated overnight at 37° C. in the presence of the virus, then the supernatant containing virions was discarded and fresh medium was added.

Seventy-two hours after infection, $2 \times 10^5$ cells were harvested, resuspended in 50 μL PBS and plated in an opaque 96-well plate (Nunc).

Then, 50 μL of D-Luciferin (0.3 mg/mL, Caliper) were added to the cells for 5 minutes, and the plate was analyzed using IVIS Lumina II.

GRANTA-519 and C-666 luciferase-transduced cells were injected s.c. in SCID mice ($5 \times 10^6$/200 μL RPMI/mouse) on day 0.

On day 7, the injected mice were randomly divided into two groups, one of which was treated with 0.3 mg/mouse of anti-BARF1 mAb weekly.

Animals were anesthetized i.p. (1-3% isoflurane, Merial Italia SpA) and injected with 150 mg/kg of D-Luciferin in PBS. Eight minutes after injection of luciferin, mice were analyzed for photon emission using IVIS Lumina II.

The same analysis was performed weekly and the average brightness of photons (expressed as p/sec/cm$^2$/sr) was evaluated.

In a different experiment, SCID mice were injected i.v. with 3×10$^6$ GRANTA-519 and C-666 luciferase-transduced cells.

Then, part of the mice was treated with 0.3 mg/mouse of anti-BARF1 mAb from day 7 and weekly thereafter.

All mice were analyzed weekly using IVIS Lumina II.

At the end of each acquisition, a photographic image was obtained.

The pseudocolor bioluminescence images are shown superimposed on grayscale mice images, with the strongest luciferase signal detected shown in red and the weaker signal shown in blue.

Statistical Analyses

For both tumor growth and bioluminescence analyses, statistical analyses were performed using the MedCalc software, version 9.4.2.0, applying each time the most appropriate tests.

Survival diagrams and survival data analysis (using the Kaplan-Meier test) were carried out with the same statistical software.

Results

Antibody Production

Conventional BALB/c mice were immunized according to a routine program with KLH-conjugated peptides (05/08, 06/08 and 08/08' of SEQ ID NO:14; FIG. 1a), and sera were collected and analyzed by ELISA.

All peptides gave high absorbance values even at very high dilution after immunization, thus demonstrating the immunogenicity of KLH-conjugated peptides.

On the other hand, since BARF1 is expressed on the surface of infected cells, we labeled the GRANTA-519 cell line, a human EBV+ mantle B-cell lymphoma cell line expressing BARF1 mRNA, with sera of mice and the analysis was conducted by flow cytometry.

After a first series of 3 vaccinations, GRANTA-519 cells were negative, which required additional vaccinations of mice before an appropriate signal was detected.

It is interesting to note that the immunoglobulin titers, as evaluated by ELISA test, remained almost at the same levels, indicating that the antibodies are already present in high titer in mice after a normal immunization program, but only after repeated vaccinations, some antibody became able to recognize epitopes naturally shaped and physiologically presented on the cell surface.

After the generation of hybridomas and the selection performed by ELISA and flow cytometry, only one clone (3D4, derived from a mouse immunized with peptide 08/08' of SEQ ID NO:14) was selected for subsequent analysis.

Isotype characterization revealed that the 3D4 antibody belongs to IgG2a immunoglobulins.

As a first BARF1 recognition test, the antibody was tested by dot blot assay: peptides used for immunization and peptides derived from peptide 08/08' of SEQ ID NO:14 and overlapping of 4-amino acids, were anchored to a PVDF membrane to identify and confirm the epitope recognized by the anti-BARF1 3D4 antibody.

Dot blot analysis revealed that the 3D4 mAb does not recognize non-linked peptides (05/08 and 06/08), while peptide 08/08' is labeled positively.

Moreover, additional peptides were created from peptides 08/08 of SEQ ID NO:10 and 08/08' of SEQ ID NO:14, ranging from AA 1 to 8 (08/08-1) of 08/08', 6-13 (08/08-2) of 08/08 and 5-11 (08/08-2') of 08/08':

| 08/08-1 | RVTLTSYW | SEQ ID NO: 11 |
| 08/08-2 | TSYWRRVS | SEQ ID NO: 12 |
| 08/08-2' | TSYWRRV | SEQ ID NO: 15 |

Only peptide 08/08-1 was recognized by the anti-BARF1 3D4 antibody, thus indicating that the recognized epitope resides in the sequence thereof (FIG. 1b).

BLAST analysis revealed that the sequence of the epitope is specific for the BARF1 protein and for the human colony stimulating factor 1 (hCSF-1), which has already been described as sharing high homology with the BARF1 protein.

In Vitro Assays

Staining by Immunofluorescence

The anti-BARF1 3D4 antibody was used to label tumor cell lines belonging to different histological types and with or without the presence of EBV infection.

Although with different staining capacity, the 3D4 clone showed the ability to stain BARF1-positive cells, while EBV-negative and BARF1-negative cells remained negative (FIG. 1c).

The differences of staining intensity observed among positive cells can be most probably attributed to the differential expression of BARF1: in fact, little information about the expression of BARF1 on the cell surface is available, so we can expect a differential protein expression on different cell lines or on the same cell line but at different culture stages (in fresh medium or in an acidified medium).

Moreover, cleavage of the extracellular domain of BARF1 has been described, although the percentage of cleavage is still to be clarified.

In order to define the specificity of the antibody for its target more precisely, we generated a BARF1-expressing cellular model: labeling of the BARF1-transduced cell line MKN-45 with anti-BARF1 3D4 mAb revealed a high positivity, compared to the BARF1-negative parental cell line (FIG. 1d), thus demonstrating the specificity of the generated antibody.

CDC and ADCC

Complement-mediated lysis (CDC) was evaluated in a standard chromium release assay. Also in this test, we used both EBV-positive and EBV-negative cell lines as target cells.

FIG. 2a shows a representative experiment, under the best experimental conditions (E:T ratio 300:1).

EBV-positive cell lines (GRANTA-519, C-666 and BL-41 B95.8) were lysed when exposed to the complement, while the lysis of the BL-41 cell line (EBV-negative cell line) was almost comparable to the background signal.

As described for the flow cytometric analysis, we observed different lysis percentages for the different target cell lines which, again, may be attributable to the differential BARF1 expression on the cell surface (FIG. 2a).

Antibody-Dependent Cell-mediated Cytotoxicity (ADCC) assays were run using the Calcein AM protocol.

Figure 2B:
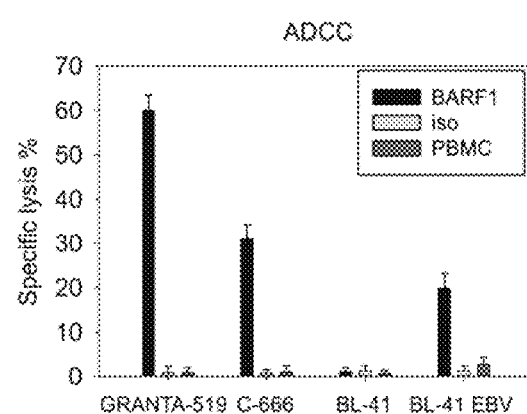
Figure 2B:
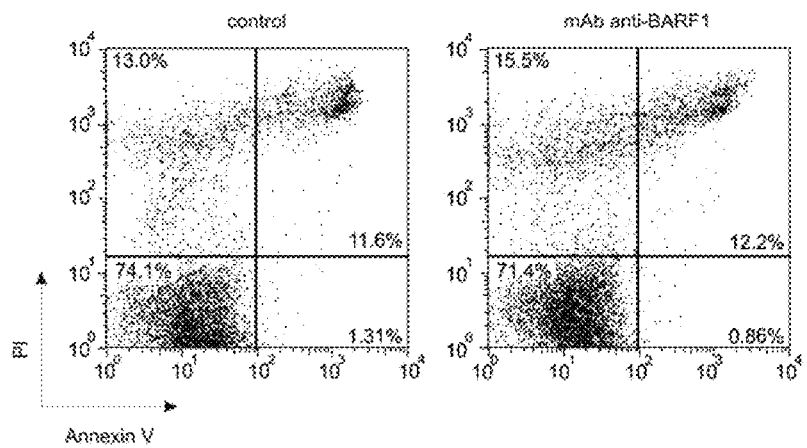

EBV-positive cells (GRANTA-519, C-666) and EBV-negative cells (BL-41) were also used for this test, while PBMC from the Buffy Coat of healthy donors were used as effector cells (FIG. 2b).

FIG. 2b is representative of the various experiments conducted.

The highest BARF1-positive cell lysis was obtained with 20 µg/mL of clone 3D4 at an effector:target ratio of 300:1.

The NK population (CD56 and CD16 positive) was evaluated in PBMCs: the percentage of NK cells was quantified between 12% and 15% of the total population.

In Vivo Assays

Biodistribution

For the biodistribution analysis, the fluorescence signal of Alexa-680-conjugated anti-BARF1 antibody was analyzed in EBV-positive and EBV-negative tumor mass-bearing mice.

Mice were injected with MKN-45 cells on one side thereof and with MKN-45 cells transduced with BARF1 on the other side thereof.

The analysis was performed daily for a week and the fluorescence intensity values for the two tumor masses were reported.

Figure 3:
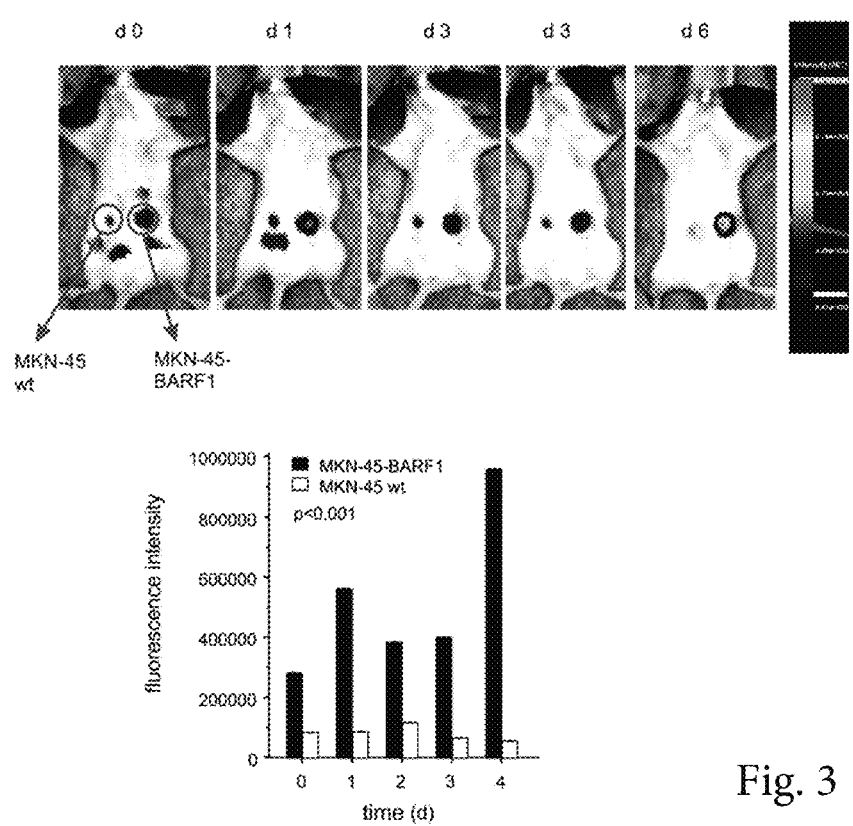
FIG. 3: Biodistribution. Statistical analysis of the fluorescence obtained from MKN-45 and MKN-45 BARF1-transduced tumor masses at different days after i.v. injection of anti-BARF1 mAb conjugated to Alexa680. The ANOVA analysis shows a statistically significant difference between the two groups (p<0.001).

Statistical analysis revealed that the 3D4 antibody accumulates specifically in the BARF1-positive tumor mass (FIG. 3, $p<0.01$).

Therapy

Tumor cell lines were injected in SCID mice to evaluate the therapeutic capacity of the anti-BARF1 3D4 antibody in a mouse model.

C-666 cells were injected subcutaneously in SCID mice and part of them were treated with the anti-BARF1 3D4 mAb.

Statistical analysis of tumor growth kinetics in treated mice compared to the controls revealed that injection of the anti-BARF1 3D4 mAb slowed down and reduced the tumor growth ($p=0.0028$, $p=0.002$ and $p=0.0026$ at days 24, 26, and 28, respectively; FIG. 4a).

After 30 days, the therapeutic effect of the treatment decreased and the C-666 tumor mass begins to grow rapidly also in the treated group.

On the contrary, in mice injected subcutaneously with the EBV-positive but BARF1-negative RAJI cells, the treatment did not result in any reduction of the tumor mass, as expected from the in vitro results.

C-666 cells were also injected subcutaneously in $RAG^{-/-}$ γ-chain$^{--}$ mice (lacking functional B, T and NK cells), but no difference was observed between the control and the treated group ($p=0.77$; data not shown), thereby indicating that the main action mode of the selected mAb is probably ADCC.

A bioluminescence model was used for the analysis of the same cell line injected through the caudal vein: in fact, C-666 cells were transduced with the enzyme luciferase and injected intravenously in mice.

The mouse tumor model was analyzed weekly with the IVIS Lumina II equipment, and the number of photons within an area of interest is the parameter used for statistical analysis.

As indicated above for the s.c. tumor growth kinetics, the progression of the C-666 tumor was slowed by the treatment with the 3D4 anti-BARF1 antibody (FIG. 4b).

Statistical analysis was performed on the average radiance (FIG. 4c), revealing a significantly reduced tumor growth in the treated group (n=12) with respect to controls (n=12) ($p<0.001$ at day 49), thus demonstrating that the anti-BARF1 3D4 antibody is endowed with therapeutic activity.

Finally, we analyzed the survival of treated and control mice, which outlined a significant improvement in the treated group compared to the control group (data not shown).

The same experiments were performed using the GRANTA-519 cell line.

In the control group, the tumor growth was fast and aggressive, while in mice treated with the 3D4 mAb it is significantly reduced ($p<0.05$ at day 21; FIG. 5a).

As already described, the same test when performed in $RAG^{-/-}$ γ-chain$^{-/-}$ mice revealed no significant difference in tumor growth, thus underlining the importance of ADCC as anti-BARF1 antibody-mediated cytotoxicity mechanism ($p=0.14$; data not shown).

Moreover, GRANTA-519 cells were transduced with the luciferase gene, injected i.v. and analyzed by bioluminescence.

Also in this context, statistical analysis of survival showed a better trend of treated mice compared to controls ($p=0.002$; FIG. 5b).

The study revealed that also in this condition, treatment with the anti-BARF1 3D4 mAb slowed the tumor spread with respect to the control group ($p<0.05$ at day 21; FIGS. 5c and 5d).

The invention claimed is:

1. A monoclonal antibody directed against BamH1-A rightward frame-1 (BARF1) comprising at least one heavy chain variable domain and at least one light chain variable domain, the at least one heavy chain variable domain VH comprising the CDR1, CDR2, CDR3 sequences encoded respectively by SEQ ID NO:3, SEQ ID NO:4 and SEQ ID NO:5, and the at least one light chain variable domain comprising the CDR1, CDR2, CDR3 sequences encoded respectively by SEQ ID NO:6, SEQ ID NO: 26 and SEQ ID NO:7.

2. The monoclonal antibody according to claim 1, wherein the at least one heavy chain variable domain comprises the amino acid sequence encoded by SEQ ID NO: 1 and the at least one light chain variable domain comprises the amino acid sequence encoded by SEQ ID NO: 2.

3. The monoclonal antibody according to claim 1, wherein the antibody comprises whole immunoglobulins or immunoglobulin fragments comprising at least one heavy chain variable domain and at least one light chain variable domain.

4. The monoclonal antibody according to claim 3, wherein the antibody comprises Fab fragments, F(ab')2 fragments, or single chain Fv fragments (scFv).

5. The monoclonal antibody according to claim 1, wherein the antibody is murine or humanized.

6. A pharmaceutical preparation comprising the antibody according to claim 1, and a pharmaceutically acceptable excipient.

7. A method for the treatment of a tumor comprising administering to a subject in need thereof a pharmacologically effective amount of the antibody according to claim 1, wherein said tumor expresses BARF1.

8. The method according to claim 7, wherein said tumor is an Epstein-Barr virus-related tumor.

9. The method according to claim 7, wherein said tumor is nasopharyngeal carcinoma (NPC), Hodgkin's lymphoma (HL), Burkitt's lymphoma, non-Hodgkin EBV+ lymphomas, post-transplant EBV+ lymphoproliferations, T-cell and NK-cell neoplasias, or gastric carcinoma (GC).

10. A method for the treatment of a tumor comprising administering to a subject in need thereof a pharmacologically effective amount of the antibody according to claim 1, wherein said tumor is nasopharyngeal carcinoma (NPC), Hodgkin's lymphoma (HL), Burkitt's lymphoma, non-Hodgkin EBV+ lymphomas, post-transplant EBV+ lymphoproliferations, T-cell and NK-cell neoplasias, or gastric carcinoma (GC) and wherein said tumor expresses BARF1.

11. A method for the treatment of a tumor comprising administering to a subject in need thereof a pharmacologically effective amount of the pharmaceutical preparation according to claim 6, wherein said tumor expresses BARF1.

12. A method for the treatment of a tumor comprising administering to a subject in need thereof a pharmacologically effective amount of the pharmaceutical preparation according to claim 6, wherein said tumor is nasopharyngeal carcinoma (NPC), Hodgkin's lymphoma (HL), Burkitt's lymphoma, non-Hodgkin EBV+ lymphomas, post-transplant EBV+ lymphoproliferations, T-cell and NK-cell neoplasias, and gastric carcinoma (GC), and wherein said tumor expresses BARF1.

* * * * *